United States Patent [19]

Kirchhoff et al.

[11] Patent Number: 4,687,823

[45] Date of Patent: Aug. 18, 1987

[54] ALKYNYL-BRIDGED POLY(ARYLCYCLOBUTENE) RESINS

[75] Inventors: Robert A. Kirchhoff; Stephen F. Hahn, both of Midland, Mich.

[73] Assignee: The Dow Chemical Company, Midland, Mich.

[21] Appl. No.: 880,778

[22] Filed: Jul. 1, 1986

[51] Int. Cl.$^4$ .............................................. C08F 267/04
[52] U.S. Cl. .................................. 526/284; 526/285; 585/26; 585/27
[58] Field of Search .................. 526/284, 285; 585/26, 585/27

[56] References Cited

U.S. PATENT DOCUMENTS 3,271,378 9/1966 Daniels ................................ 526/285
4,540,763 9/1985 Kirchhoff ............................ 526/284

Primary Examiner—Paul R. Michl
Assistant Examiner—Peter D. Mulcahy

[57] ABSTRACT

Arylcyclobutene resins are comprised of alkynyl groups bridging at least two arylcyclobutene moieties.

16 Claims, No Drawings

ALKYNYL-BRIDGED POLY(ARYLCYCLOBUTENE) RESINS

BACKGROUND OF THE INVENTION

This invention relates to poly(arylcyclobutene) monomers, oligomers, prepolymers and polymers.

Arylcyclobutene resins are a family of monomers, oligomers, prepolymers and polymers which exhibit high thermal stability and resistance to oxidative and chemical degradation. Poly(arylcyclobutene) polymers are disclosed in U.S. Pat. No. 4,540,763. Such polymers can have a variety of bridging groups connecting the arylcyclobutene moieties. The properties of the polymer are affected by the different bridging groups. For example, the polymer can be fire resistant if the bridging group contains a halogen, such as bromine. In another example, the polymer can be electro-insulative if the bridging groups contain inorganic atoms, such as silicon.

It would be desirable to have arylcyclobutene resins which can form a graphite-like substance upon being subjected to carbonization.

SUMMARY OF THE INVENTION

This invention is an arylcyclobutene monomer having two arylcyclobutene moieties bridged by an alkynyl molecular group.

In another aspect, this invention is an arylcyclobutene polymer comprising, in polymerized form, an arylcyclobutene monomer having two arylcyclobutene moieties bridged by an alkynyl molecular group.

The monomers, oligomers, prepolymers and polymers of this invention can provide synthetic graphite-like substances upon being subjected to carbonization. The monomers and polymers are useful in many thermoset resin applications, especially in the manufacture of composites which find graphite fibers useful.

DETAILED DESCRIPTION OF THE INVENTION

The arylcyclobutene moieties useful in this invention are disclosed in U.S Pat. Nos. 4,540,763; 4,562,280; and 4,570,011, all herein incorporated by reference. The arylcyclobutene moieties are bridged by an alkynyl molecular group. An alkynyl molecular group is a group of at least two carbon atoms bonded by a triple bond. The molecular group can be comprised of other atomic and molecular groups. Preferably, the alkynyl molecular group is comprised of hydrocarbon groups, and most preferably is exclusively an alkynyl group (i.e., an acetylenic group), or a hydrocarbon bridged bis-acetylenic group.

The ideal arylcyclobutene monomers can be represented by the formula

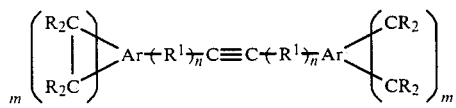

wherein
Ar is an aromatic moiety;
R is, independently, hydrogen, an electron-donating moiety or an electron-withdrawing moiety;
$R^1$ is, independently, a polyvalent organic group or a polyvalent inorganic group;
m is an integer of at least 1; and
n is independently either 0 or 1; provided that when n is 0, then the vicinal alkynyl carbon is directly bonded to the aromatic moiety.

The most preferred aromatic moiety is a benzene moiety. Therefore, a highly preferred arylcyclobutene monomer of this invention, wherein both n's are 0, is an acetylene bridged benzocyclobutene monomer which can, ideally, be represented by the formula

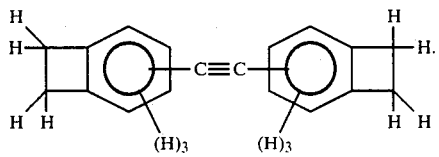

In yet another highly preferred arylcyclobutene monomer of this invention, the alkynyl group is a phenyl bridged bis-acetylenic group. This monomer has one n as 0, the other n as 1, and that $R^1$ as a phenyl-acetylene moiety which corresponds to the formula

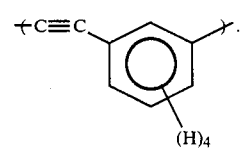

This monomer can ideally be represented by the formula

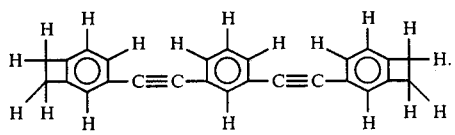

Still yet another highly preferred monomer is the dimer of 4-acetylene benzocyclobutene. In such a monomer, the alkynyl group is a bis-acetylene group. The dimer can be prepared according to processes similar to those described in G. Eglenton and A. R. Galbraith, Journal Chemical Society, 889, 1959; S. Akiyama and M. Nakagawa, Bulletin of Chemical Society of Japan 33, 1291, (1960); and A. S. Hay, Journal of Organic Chemistry, 25, 1275, 1960. For example, the 4-acetylene benzocyclobutene can be contacted with a catalytic amount of a suitable copper catalyst, such as cupric acetate (i.e., $(CH_3COO)_2Cu$) in the presence of pyridine and air (i.e., $O_2$). Such a monomer can ideally correspond to the formula

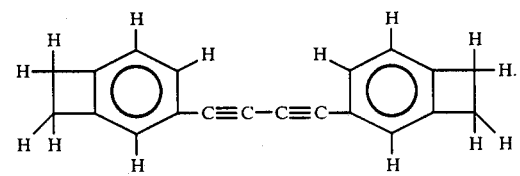

The alkynyl-bridged arylcyclobutene monomers can be prepared by heating an alkenyl-bridged arylcyclobutene monomer in the presence of a compound useful for removing the hydrogens on a double bond. A preferred compound is pyridinium hydrobromide perbromide. The reaction product is then heated in the presence of a mixture useful for forming triple-bonded carbons. A preferred mixture is triethylene glycol and potassium hydroxide. The alkynyl-bridged arylcyclobutene monomer can then be recovered by suitable means, such as solvent extraction in methylene chloride.

In yet another method, an alkynyl-arylcyclobutene compound can be contacted with a halogenated compound in the presence of a palladium catalyst.

As used herein, "polymers" means two or more monomers bonded together. Included in the term are dimers, oligomers, and prepolymers. The arylcyclobutene monomers can be polymerized by subjecting the monomers to suitable polymerization conditions (i.e., conditions under which the cyclobutene ring opens). Preferred conditions are subjecting the monomers to heat. Suitable temperatures include between about 200° C. and about 275° C., preferably about 250° C. Suitable time periods are from about 30 minutes to several hours.

The alkynyl-bridged arylcyclobutene polymers can be usefully pyrolyzed to form a graphite-like substance. The pyrolysis of the polymers can cause the substantial carbonization of the polymers. The pyrolyzed acetylene-bridged bis-benzocyclobutene can exhibit a 20 percent weight loss in air at 600° C., and does not exhibit any greater weight loss above 600° C.

The following examples are provided as illustrations of the invention, and do not limit the scope thereof.

EXAMPLES

EXAMPLE 1

Preparation of Acetylene-Bridged Bis-Benzocyclobutene Monomers

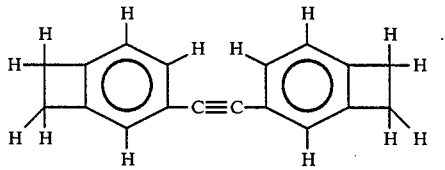

In a 50 ml flask equipped with a reflux condenser, nitrogen bubbler and magnetic stirrer is placed 20 ml of acetic acid. To this is added 0.40 g (0.0017 moles) of 1,2-bis(4-benzocyclobutenyl)ethylene. The mixture is then heated to 100° C. until everything is dissolved. While still at 100° C., 0.60 g (0.0019 moles) of pyridinium hydrobromide perbromide is added and the mixture is heated for another hour at 100° C. and then cooled to room temperature. The solid product is filtered off, worked with acetic acid and transferred to a 25 ml flask equipped with a reflux condenser, nitrogen bubbler and magnetic stirrer. To this is then added 10 ml of triethylene glycol and 0.75 g (0.0013 moles) of potassium hydroxide. The mixture is then stirred and heated under nitrogen at 155° to 160° C. for 1 hour. It is then cooled to room temperature and poured into 100 ml of water. The mixture is extracted with methylene chloride and the methylene chloride is then worked successively with water, 5 percent aqueous hydrochloric acid, water, saturated aqueous sodium bicarbonate and lastly water. The methylene chloride layer is then dried over anhydrous magnesium sulfate, filtered and concentrated under vacuum to yield the solid product. This is then recrystallized from a mixture of pentane and toluene to yield 0.20 g of the monomer.

EXAMPLE 2

Polymerization of Acetylene-Bridged Bis-Benzocyclobutene Monomer

A 0.10 g sample of the monomer prepared in Example 1 is placed in a test tube and blanketed with a nitrogen atmosphere. The tube is placed in a heating bath at 100° C. and the temperature raised to 250° C. over 60 minutes. It is then held at 250° C. for 2 hours and then cooled to room temperature. The dark red sample of solid polymer is removed and examined by thermogravimetric analysis (TGA). The polymer shows a 5 percent weight loss at 512° C. when heated under nitrogen.

EXAMPLE 3

Preparation of Meta-Phenylene Bis-Acetylene-Linked Bis-Benzocyclobutene

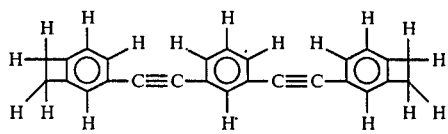

This reaction is carried out in a 250 ml three neck flask, which is equipped with magnetic stirring, a reflux condensor topped with a gas inlet tube and supplied with a positive pressure of $N_2$ via mineral oil bubbler, a thermometer, and stopper. To this apparatus is added 3.68 g meta-dibromo benzene (M.W.=235.92, Aldrich Chem., 0.0156 mole), 0.55 g bistriphenylphosphine palladium (II) dichloride (M.W.=702 g, Aldrich Chem., 0.5 mole percent, 0.00078 mole), 0.55 g cuprous iodide, (Aldrich Gold Label, M.W.=190.44 g), 1.98 g triphenyl phosphine (M.W.=262.3 g, 0.0075 mole), and 100 ml triethyl amine. This reaction is then supplied with a heating mantle, and the mixture is heated to reflux. After two hours, a large portion of grey precipitate is formed and the mixture is refluxed overnight. The reaction is stopped after 16 hours total, and when cool, the mixture is poured into 600 ml 5 percent HCl. The precipitate which forms is dissolved in 200 ml $CH_2Cl_2$, and this solution is washed with 100 ml $H_2O$, 100 ml 5 percent HCl, and 100 ml $H_2O$. The precipitate is then washed with ethanol and dried under vacuum to give 2.3 g brown material. A 0.5 g sample of this material is filtered through a 5"×1" bed of alumina with 100 ml 9:1 pentane/$CH_2Cl_2$ followed by 200 ml 8.5:1.5 pentane/$CH_2Cl_2$. Removal of the eluent by rotary evaporation gave a white powder, weight 0.34 g. This compound melts at 117°-120° C. on a Fisher-Johns melting point apparatus.

What is claimed is:

1. An arylcyclobutene monomer having two arylcyclobutene moieties bridged by an alkynyl molecular group.

2. The monomer of claim 1, wherein the arylcyclobutene moieties are benzocyclobutene moieties.

3. The monomer of claim 2, wherein the alkynyl molecular group is an acetylenic group.

4. The monomer of claim 3, corresponding to the formula

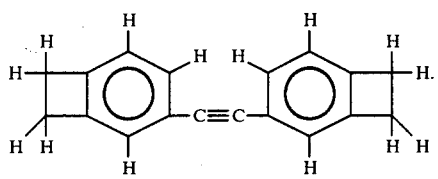

5. An arylcyclobutene polymer, comprising in polymerized form an arylcyclobutene monomer having two arylcyclobutene moieties bridged by an alkynyl molecular group.

6. The polymer of claim 5, wherein the arylcyclobutene moieties are benzocyclobutene moieties.

7. The polymer of claim 6, wherein the alkynyl molecular group is an acetylenic group.

8. The polymer of claim 7, wherein the monomer corresponds to the formula.

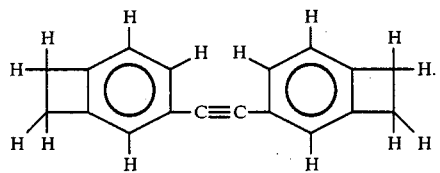

9. The monomer of claim 2, wherein the alkynyl group is a phenyl bridged bis-acetylenic group.

10. The monomer of claim 9, corresponding to the formula.

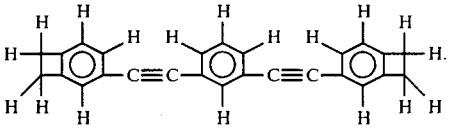

11. The polymer of claim 6, wherein the alkynyl group is a phenyl bridged bis-acetylenic group.

12. The polymer of claim 7, wherein the monomer corresponds to the formula

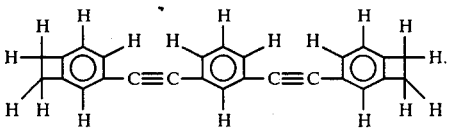

13. The monomer of claim 2, wherein the alkynyl group is a bis-acetylene group.

14. The monomer of claim 13, corresponding to the formula

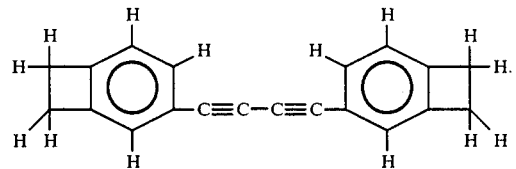

15. The polymer of claim 6, wherein the alkynyl group is a bis-acetylene group.

16. The polymer of claim 7, wherein the monomer corresponds to the formula

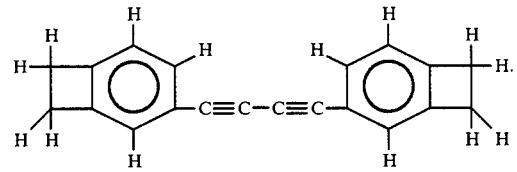

* * * * *